US006188407B1

United States Patent
Smith et al.

(10) Patent No.: US 6,188,407 B1
(45) Date of Patent: Feb. 13, 2001

(54) RECONFIGURABLE USER INTERFACE FOR MODULAR PATIENT MONITOR

(75) Inventors: Kathy K. Smith; Richard Medero, both of Tampa, FL (US); Edward V. Cruz, Newbury Park; David W. Hoard, Sherman Oaks, both of CA (US); Brian L. Pate, Tampa; Robert S. Wallace, III, Lutz, both of FL (US)

(73) Assignee: Critikon Company, LLC, Tampa, FL (US)

( * ) Notice: Under 35 U.S.C. 154(b), the term of this patent shall be extended for 0 days.

(21) Appl. No.: 09/034,800

(22) Filed: Mar. 4, 1998

(51) Int. Cl.[7] ................ G06F 13/00; G06F 17/60
(52) U.S. Cl. .............. 345/353; 345/902; 345/970; 705/2; 705/3
(58) Field of Search ................ 345/352, 353, 345/334, 339, 354, 902, 970; 705/2, 3

(56) References Cited

U.S. PATENT DOCUMENTS 4,989,610 * 2/1991 Patton et al. ............. 128/695
5,007,429 * 4/1991 Treatch et al. ............ 128/677
5,210,554 * 5/1993 Cornsweet et al. ........ 351/206
5,426,723 * 6/1995 Horsley ................... 395/128
5,819,741 * 10/1998 Karlsson et al. .......... 128/710

* cited by examiner

*Primary Examiner*—Ba Huynh
(74) *Attorney, Agent, or Firm*—Woodcock Washburn Kurtz Mackiewicz & Norris LLP

(57) ABSTRACT

A reconfigurable user interface for a modular patient monitor which selectively populates menus for operator selection based on the parameters which are available at any given time. Due to event processing, when a parameter module is added or removed from the system, the reconfigurable user interface is updated immediately to reflect the addition or subtraction of the associated parameter. A flash box in each menu provides shortcuts to the most likely menu option in response to asynchronous events such as alarms and the like. The flash box also assists the operator with the particular steps that must be followed to properly setup or operate a particular feature of the system. Since the menus are not modal, an operator may navigate the menus without making any selections or changing the state of the device.

20 Claims, 7 Drawing Sheets

FIG. 3
AUXILLARY SCREEN

RECONFIGURABLE USER INTERFACE FOR MODULAR PATIENT MONITOR

BACKGROUND OF THE INVENTION

1. Field of the Invention

The present invention relates to a reconfigurable user interface for a modular patient monitor, and more particularly, to a user interface which recognizes when new parameter modules and parameters are added to or removed from the patient monitor, automatically reconfigures the monitor's display to display the new parameters, and automatically updates the menu selection options for the display. A flash box on the menu is activated by certain conditions to allow rapid navigation to the most likely menu item to be selected.

2. Brief Description of the Prior Art

Conventionally, each patient in a hospital bed may have his or her vital signs monitored by a multi-parameter monitor. Such monitors are typically preconfigured to monitor certain parameters only and may not be capable of monitoring all of the necessary parameters for a particular patient. For example, every patient may or may not have an invasive line that needs monitoring. With a modular patient monitor, a single invasive pressure module can be shared among multiple monitors because it is very unlikely that more than one patient will require invasive pressure monitoring at any one time. Accordingly, a modular patient monitor, known as the DINAMAP™ MPS Select Monitor, has been developed by the present assignee to monitor patients in acute care settings such as critical care, emergency room, radiology, labor and delivery, and the operating room whereby each monitor may be reconfigured by adding or subtracting parameter modules. Using this monitor, an operator can view, record, and recall clinical data derived from each patient parameter. Separate, removable parameter modules mate with the main processor during use to selectively, and simultaneously, collect patient data such as end tidal $CO_2$ respiration rate, the patient's heart rate, the patient's blood pressure (invasive and noninvasive), the patient's temperature, the patient's electrocardiogram, the oxygen saturation ($SpO_2$) of the patient's arterial blood, and/or the patient's respiration rate.

This monitor is specifically designed to accept many different combinations of parameter modules so that the monitor is completely reconfigurable to handle the specific monitoring needs of a particular patient. For example, the monitor may accept up to nine different parameter modules, where each module measures one or more different patient parameters. As a result, a separate monitor for each parameter is unnecessary, and it is also unnecessary to provide an additional expensive multi-parameter unit when only a few patient parameters need to be monitored.

Since the DINAMAP™ MPS Select Monitor needs to monitor multiple parameters from multiple modules, a modified input/output interface is needed which determines which parameter module is connected, in which port the parameter module is connected, and which parameters need to be communicated to/from the display processor. Since the parameter modules may be added and removed at any time, whether the monitor is on or off, it is desired that the input/output interface immediately detect a changed configuration and promptly adapt to the new configuration automatically. Also, the input/output interface should allow rapid navigation to those items most likely to be selected from the options menu, so as to save time in potentially life-saving situations. The present invention has been designed to meet these needs.

SUMMARY OF THE INVENTION

The present invention satisfies the above-mentioned needs in the art by providing a reconfigurable user interface for a modular patient monitor which automatically adapts to a new configuration of parameter modules and parameters and displays the new parameters to the operator in a new display configuration. Such a modular patient monitor in accordance with the invention preferably comprises a display which displays patient parameter data, a parameter interface which determines the patient parameters for which patient monitoring is activated, as by the insertion of the associated parameter module, and which accepts patient parameter data for presentation on the display, and a display processor which processes the patient parameter data from the parameter interface to determine which and how many patient parameters need to be displayed on the display, which allocates space on the display for vital signs and/or waveform data associated with the patient parameters to be displayed, and which automatically reallocates space for presentation of the patient parameter data on the display. The reallocation is determined using parameter settings based on operator preferences regarding the appearance on the display of the vital signs and/or waveform data associated with the patient parameters and occurs when a patient parameter is activated or deactivated, as by insertion or removal of a parameter module, during operation of the modular patient monitor. Preferably, an off-line parameter is brought into a ready state upon detection of connection of a sensor to the parameter module and from the ready state to an operating state when patient parameter data from the parameter interface is detected.

The display processor of the invention includes menu manager software which presents menus to the display for user navigation and which automatically updates menu selection options in the menus when the parameter interface provides an indication that a patient parameter has been activated or deactivated. Preferably, a parameter setup secondary menu is added as a menu selection option when an associated patient parameter is activated and is removed as a menu selection option when the associated patient parameter is deactivated. Preferably, the menu system is not modal in that the operator is not forced to make a decision or selection before changing menus and thus can explore parameter settings without changing them. Also, to maximize screen usage, a menu preferably closes after a predetermined period of inactivity of the select knob.

In accordance with another aspect of the invention, each menu contains a flash box which flashes a most likely menu selection item for selection from the menu in response to an asynchronous patient monitoring event, such as an alarm, which is detected by the parameter interface. In response to such an asynchronous patient monitoring event, the menu manager preferably places a menu selection cursor at the flash box for selection of the most likely menu selection item without further cursor movement, thereby minimizing navigation. Typically, the asynchronous patient monitoring event is a condition of the monitor, such as an alarm, requiring operator attention, and the most likely menu selection option is a menu selection option which services the condition (e.g., services the alarm condition). A plurality of such asynchronous patient monitoring events may be kept in a queue for handling in a first in, first out fashion.

In accordance with still another aspect of the invention, the patient monitor includes a parameter module which plugs into a main housing of the patient monitor so as to activate a patient parameter associated with the parameter module. Preferably, the display processor displays a graphic of the patient monitor on the display and overlays on the graphic of the patient monitor a graphic of each type of parameter module which is plugged into the main housing. A graphic of a sensor associated with an activated patient parameter is also provided which is highlighted when an operator is setting parameter settings for the activated patient parameter.

In accordance with the invention, each patient parameter preferably has a parameter settings table which specifies factory default, operator default, and active parameter settings regarding the appearance on the display of the vital signs and/or waveform data associated with that patient parameter. The operator default parameter settings are those set by an operator in a display configuration mode while the active parameter settings are those set by an operator during active monitoring of a patient. Preferably, a copy of the parameter settings table for the activated patient parameter is stored in a memory of the parameter module and in a memory of the main housing, and in the case of inconsistencies in the parameter settings stored in the memory of the parameter module and in the memory of the main housing, the display processor prompts the operator to select which parameter settings to use. In the preferred embodiment of the invention, the active settings are stored in the memory of the main housing when the patient monitor is turned off, whereby the monitor may use the same settings when it is turned back on. In this case, the operator settings are only copied over active settings in response to an operator initiated event such as a request to admit a new patient. Such operator default parameter settings preferably include an operator's priority of the importance of respective patient parameters for display. This enables the vital signs and/or waveform data associated with higher priority patient parameters to be displayed more prominently on the display. The waveform data may be further sorted by membership priority (i.e., in the set of waveforms to be displayed) as well as location priority (e.g., highest priority waveforms are displayed at the top of the display).

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings of which:

FIG. 3 illustrates the auxiliary screen including a trends menu.

DETAILED DESCRIPTION OF PRESENTLY PREFERRED EMBODIMENTS

A reconfigurable user interface for a modular patient monitor with the above-mentioned beneficial features in accordance with a presently preferred exemplary embodiment of the invention will be described below with reference to FIGS. 1–7. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

Figure 1:
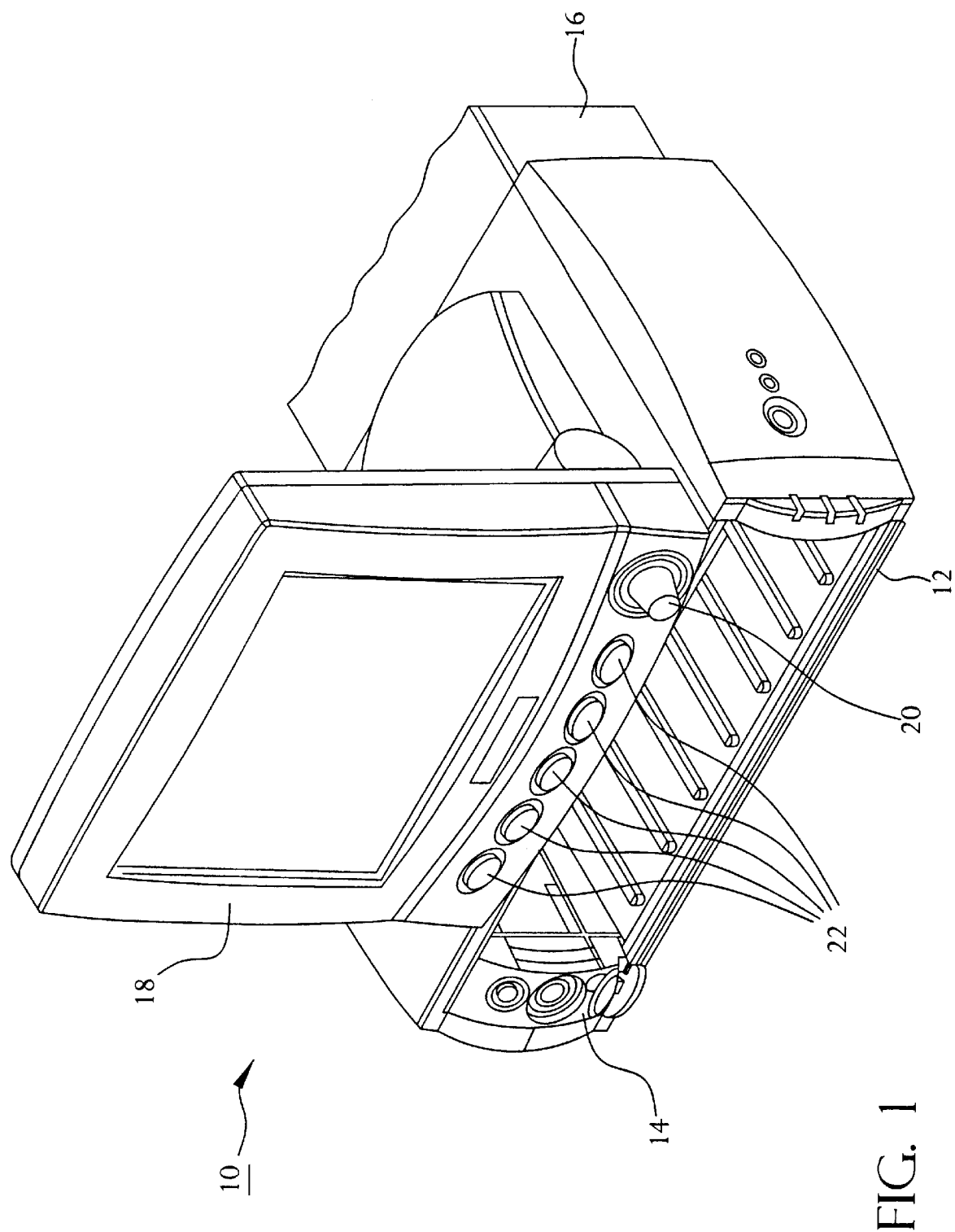
FIG. 1 is a perspective view of a multi-parameter modular patient monitor which includes a reconfigurable user interface in accordance with the invention.

FIG. 1 is a front perspective view of a modular patient monitor 10, such as the DINAMAP™ MPS Select Monitor sold by the present assignee, which accepts parameter modules in accordance with a preferred embodiment of the invention. As shown in FIG. 1, the modular patient monitor 10 includes a main housing 12, which functions as a connection receptacle for a plurality of (e.g., nine) parameter modules 14, a housing for a display processor 16, and an articulating display 18. The parameter modules 14 are respective electronics modules which mate with the modular patient monitor 10 via the main housing 12 during use to selectively monitor a patient's vital signs and patient airway gases and to provide thermal paper strip records of same. Parameter modules 14 process data from transducers (not shown) to generate waveforms and numeric vital signs data which is then processed in display processor 16 for display on display 18. Recorder modules generate the same information on a printout, as desired.

All parameter modules 14 can be inserted or removed, as necessary, while the modular patient monitor 10 is operating. If a new parameter module 14 is inserted, the modular patient monitor 10 of the invention automatically detects its new configuration and displays the new parameter of the new parameter module 14 as an option on the display 18. The waveforms and parameter measurements displayed on display 18 thus vary according to the parameter modules 14 inserted into the main housing 12. A patient may continually be monitored with any of the remaining parameter modules 14 while another parameter module 14 is being inserted or removed. Modular patient monitor 10 accepts a variety of different combinations of parameter modules 14, where the parameter modules preferably collect patient parameter data such as $CO_2$ exhaled by the patient, the patient's heart rate, the patient's blood pressure (invasive and noninvasive), the patient's temperature, the patient's electrocardiogram, the oxygen saturation ($SpO_2$) of the patient's arterial blood, and/or the patient's respiration rate.

The modular patient monitor 10 automatically detects the insertion or removal of a parameter module 14 and updates its configuration automatically so that only the waveform and numeric vital signs data for the connected parameter modules 14 are displayed on the display 18. Such a modular patient monitor 10 employing removable parameter modules 14 which enable the modular patient monitor 10 to be reconfigured by the operator in the field preferably includes a robust blind mating mechanism which ensures reliability of the modular patient monitor 10 in the hostile environment in which such a modular patient monitor 10 may be used. Modular patient monitor 10 also includes a circuit which detects the presence of each module and a communication system which monitors the status of the parameters from connected parameter modules 14 by noting which parameter module 14 is connected, in which port of the main housing 12 the parameter module 14 is connected, and determining which parameters need to be communicated to/from the display processor 16, where it is noted that each parameter module 14 can contain one or more logical parameters. A parameter network provides communications between the display processor 16 and separate parameter modules 14 which may, in turn, have their own microprocessor to control the transfer of parameter data or may have a hardware (ASIC) implementation of the parameter communications protocol.

The parameter electronics within each parameter module 14 communicates with the display processor 16 via a parameter network I/O interface which acts as the object-oriented interface between each parameter module 14 and the rest of the modular patient monitor 10. The parameter network I/O interface sees network objects and parameter objects and communicates these objects to/from the display processor 16 and the respective parameter modules 14 over a serial parameter bus. Generally, the parameter network I/O interface is less concerned with keeping track of which parameter modules 14 are connected than with keeping track of which parameters are active for processing at any given time. An event queue informs the parameter network I/O interface of events that need to be serviced, and the waveform and numeric data associated with such events are transmitted bi-directionally over the parameter network bus in "chunks" of data defining objects which can be created and deleted to access data from each parameter.

Preferably, the parameter network I/O interface is implemented as control software which runs on the display processor 16. The reconfigurable user interface display function of the invention as described herein may also run on display processor 16 along with the parameter network control software or it may run on a dedicated display processor.

During normal operation of the modular patient monitor 10 of the invention, the display processor 16 continuously scans all parameters at a rate of 10 scans per second. Parameter scanning is accomplished by the display processor 16 by sending a data polling command message to a parameter module 14 and the parameter module 14 sending a data polling response message in return. If the display processor 16 does not see the start of a response within, e.g., 5 milliseconds, the display processor 16 considers the parameter module 14 to be inoperative and drops it and all its associated parameters from the normal scan list. Received waveform and numeric vital signs data from the parameter modules 14 is processed for display on the display 18 as will be described in more detail below.

As shown in FIG. 1, display 18 is a monochrome or color monitor which preferably rotates and tilts for optimal viewing of the waveform and numeric vital signs data received from the display processor 16. Display 18 can display, for example, a maximum of six parameter waveforms, many parameter values, and multiple menus. Alarms for both the patient and the modular patient monitor 10 are preferably sounded from the display 18. Select knob 20 is a rotary knob with push-button action. Rotating select knob 20 allows the operator to navigate through the menus, while pushing select knob 20 turns on the modular patient monitor 10 and allows the operator to select menu options. Push-button hardkeys 22, on the other hand, activate a specific function. For example, assuming the corresponding parameter module 14 (as needed) is inserted into the main housing 12, hardkeys 22 may suspend the audible indication of patient and procedural alarms for a user-selectable period of time, record waveforms and print them at the recorder parameter module 14 or a central station strip printer, capture several seconds of waveforms on the display 18, start and stop determinations of noninvasive blood pressure, or start and stop several minutes of repeated "stat" mode noninvasive blood pressure determinations.

Figure 2:
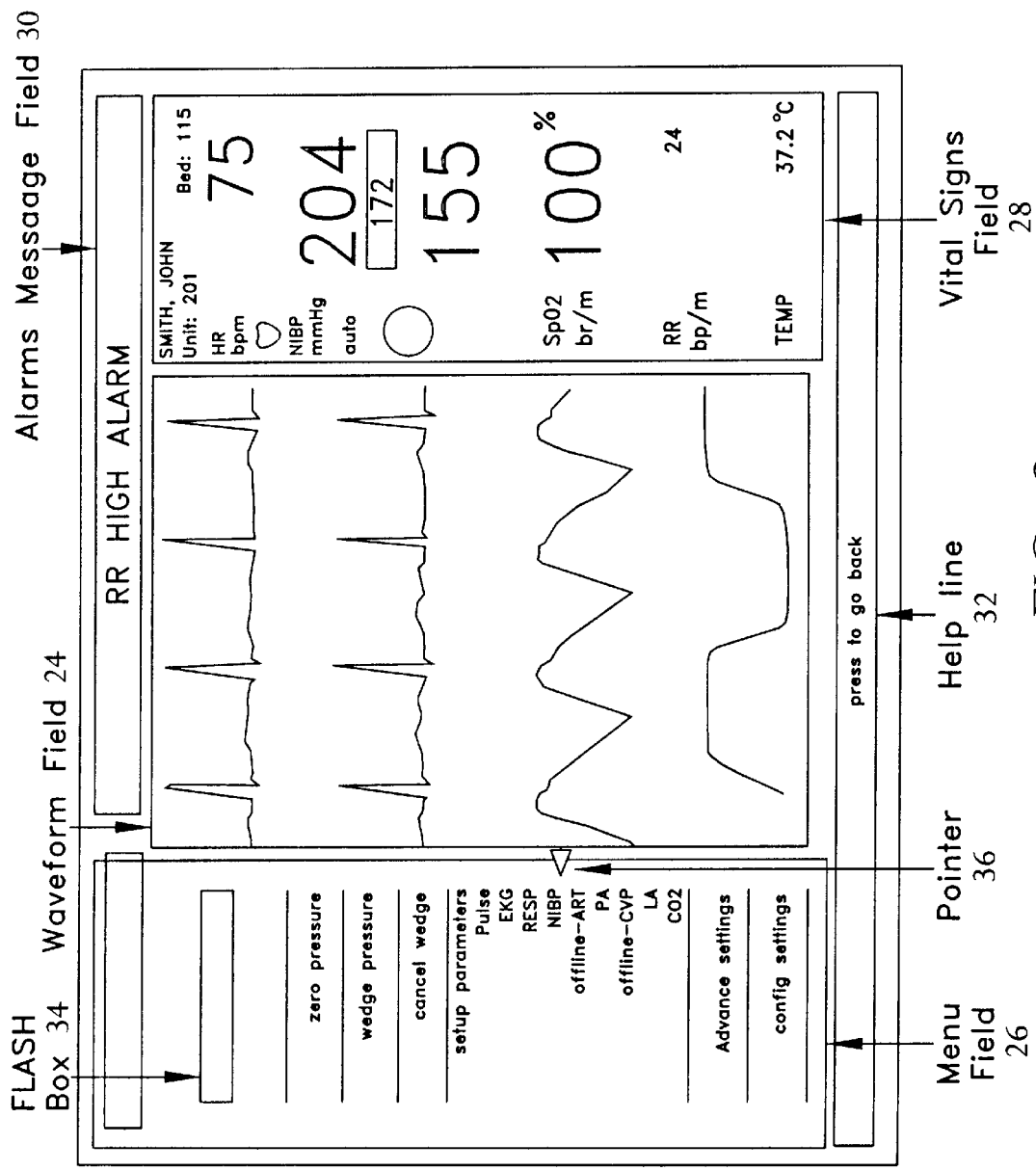
FIG. 2 illustrates the display screen of the multi-parameter modular patient monitor of FIG. 1, including an illustration of the menu field, flash (select) box, alarms message field, waveform field, vital signs field, and help line.
Figure 3:
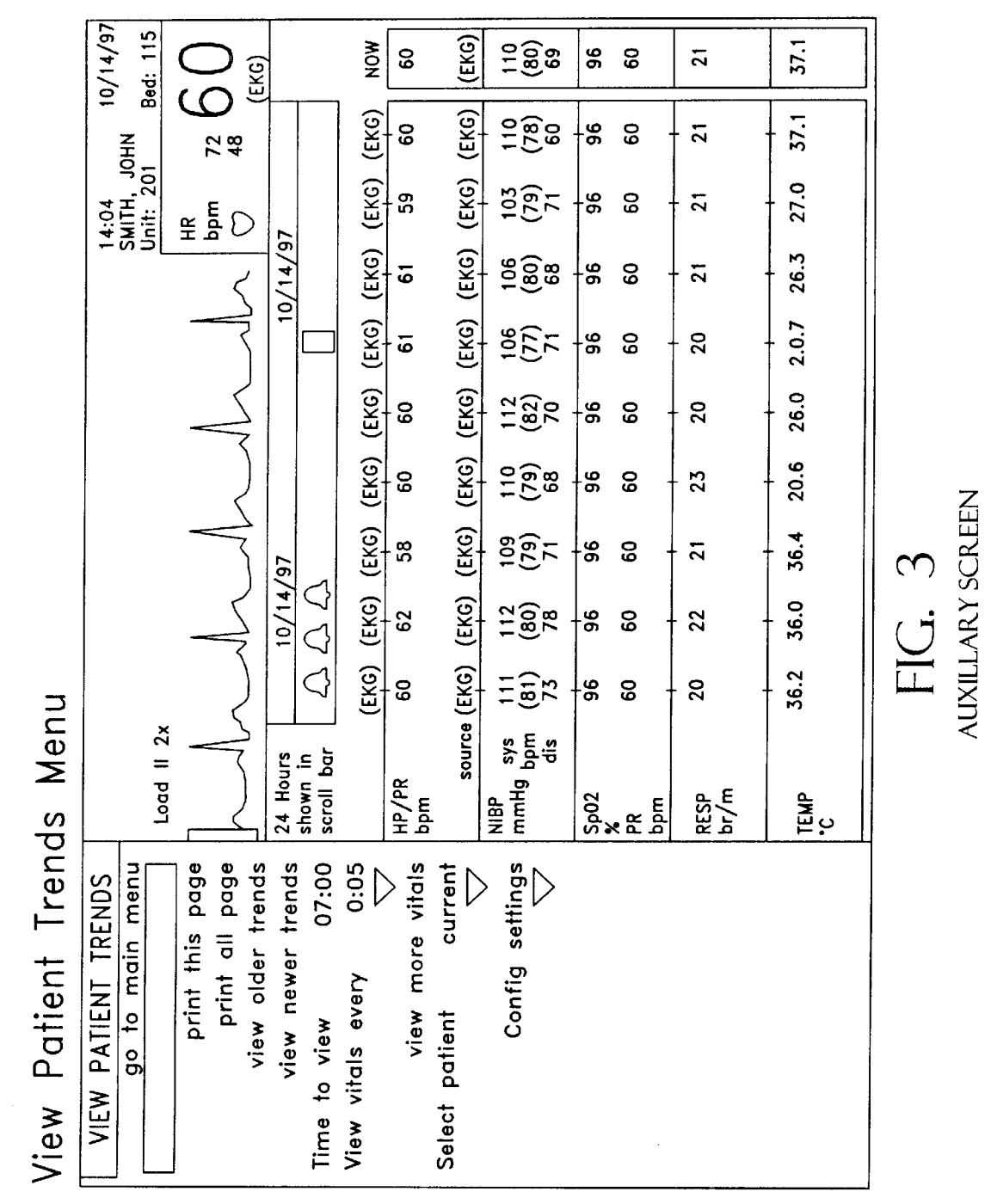

During normal operation, at least four types of screens may be displayed on the display 18 including a waveform screen, a menu screen, a trends screen, and a popup window screen. The waveform screen shows current patient data including parameter waveforms, vital signs, help lines, and alarm messages for the inserted parameter modules 14. The menu screen shows the same information as the waveform screen with the addition of a menu, which allows the operator to change current parameter settings and to perform multiple tasks, as described in detail below. As shown in FIG. 2, the menu screen includes waveform field 24, menu field 26, vital signs field 28, alarms message field 30 for displaying alarm messages, help line 32 which explain what will happen if the select knob 20 is pushed to select the menu option currently pointed to, a flash (select) box 34, and a pointer 36 to the current selection option which allows the operator to change current parameter settings and to perform multiple tasks. The trends screen, illustrated in FIG. 3, is an auxiliary screen which may be used to display trend data, alarm history data, or battery information. As illustrated in FIG. 3, the auxiliary screen continues to display the top waveform and vital signs information while using the remainder of the screen to display other information such as patient trends. Finally, the popup window screen 38 (FIG. 7) preferably covers the bottom portion of the screen until the operator responds to the displayed message and presses the select knob 20. Popup window screen 38 gives a command to the operator, asks a question, or provides information to the operator relevant to any circumstance that must be acknowledged.

As will be explained in more detail below, the main menu and any secondary menus offer multiple menu options that activate system functions of modular patient monitor 10. The setup of the menu options changes in accordance with the invention when only one of the following circumstances occurs: one or more additional parameter modules 14 are inserted into main housing 12, one or more additional parameter modules 14 are removed from main housing 12, or a current parameter module 14 is replaced with a new parameter module 14. The sequence and number of parameters shown on the display 18 are determined by display processor 16 in accordance with the number of parameter modules 14 currently in the main housing 12. Menu options that are appropriate to each parameter appear and disappear when the parameter modules 14 are inserted or removed. In particular, upon connection of a new parameter module 14, its output parameter data is displayed in accordance with configuration default settings for that parameter. Preferably, the appropriate setup parameter menu option is automatically added to the main menu and a waveform display area and vital signs display area are allocated as appropriate. The parameter remains in off-line mode, indicated by a message in the dedicated waveform area, until patient data is detected. Display processor 16 automatically switches the parameter to operate mode when patient data is detected.

The display processor 16 recognizes three different modes for the respective parameters:

off-line mode: parameter module 14 is present; no patient data is being collected; and no portion of the display 18 is dedicated to the parameter.

ready mode: parameter module 14 is present; no patient data is being collected; parameter labels are displayed; and a portion of the display 18 is dedicated to the parameter. The parameter remains in ready mode until patient data is detected.

operate mode: parameter module 14 is present; alarms are in ready mode; and patient data is detected and displayed on display 18.

Individual parameters can be placed off-line, and the monitoring of all parameters can be temporarily suspended by the operator electing to put the whole modular patient monitor 10 (including all parameters) in standby.

The behavior for all parameters in these modes may be described as follows.

A parameter in the off-line mode is analogous to its parameter module 14 not being connected. Derived vital signs are not checked against user-set limits and status alarm conditions detected by the parameter module 14 and its hardware are ignored. No portion of the vital signs field 28 is allocated for that parameter nor is a portion of the waveform field 24 allocated for that parameter. In the Setup Parameters mini menu 42 in the main menu, the parameter is identified as being off-line. If a parameter in operate or ready mode is put off-line, any active alarms for that parameter will be removed, including crisis alarms that may not have been acknowledged.

When a parameter is in ready mode, derived vital signs are not checked against user set limits, and status alarm conditions detected by the parameter module 14 and its hardware do not generate alarms. A portion of the vital signs field 28 is allocated to that parameter; however, dashes may appear in the vital sign field 28 to indicate patient data that is currently being ignored. A portion of the waveform field 24 is only allocated if the parameter was previously configured to have its waveform on. However, if allocated, no waveform signal data is displayed. If any status conditions are being detected, including those which would generate an alarm in operate mode, the associated status message will appear in the waveform field 24. Otherwise "READY" will appear in the waveform field 24. The parameter's title will appear in the Setup Parameters mini menu 42 in the main menu and its setup (secondary) menu will become accessible.

When a parameter is in operate mode, derived vital signs are checked against operator set limits and status alarm conditions detected by the parameter module 14 and its hardware generate the appropriate alarms. In other words, all alarms for that parameter are being monitored. The vital signs field 28 is allocated and data from the parameter module 14 is displayed accordingly. If a portion of the waveform field 24 is allocated, signal data is displayed along with any waveform messages, which may or may not be alarms. The parameter's title will appear in the Setup Parameters mini menu 42 in the main menu and its setup menu will be accessible.

When a parameter module 14 is initially plugged into the main housing 12, if no sensor is connected, the parameter will remain off-line. However, upon detection of a sensor/transducer, the parameter will automatically switch to the ready mode. Then, upon detection of valid patient data, the parameter will automatically switch to the operate mode. A parameter which is off-line will also automatically switch to ready mode if its setup menu is opened by the operator. In addition, using the "turn parameter off" menu choice in the secondary menu, if the operator turns off a parameter in operate or ready mode (into off-line mode), it will only be "armed" to automatically switch back into ready mode if the parameter detects a sensor disconnection. If put into ready mode by selecting the parameter's setup menu, it will switch to the operate mode upon detection of valid patient data. On the other hand, if a parameter's module 14 is disconnected for any reason, the parameter will be put into the off-line mode and its associated entry in the Setup Parameters mini menu 42 in the main menu will be removed so that its setup menu is no longer accessible.

The vital signs displayed in vital signs field 28 are managed by a vital signs manager which is a software process of display processor 16 that is responsible for displaying all of the vital signs associated with parameters in ready or operate mode. The vital signs are displayed top to bottom based on their assigned priority, where the one assigned the highest priority is displayed at the top. Generally, vital signs are assigned priorities based on the order the operator ranked all of the parameters in terms of importance in configuration mode. Since heart rate or pulse is so important and it can be derived from multiple parameters, it is automatically assigned the highest priority. Each different vital sign can be displayed in two different formats: small and large.

The vital sign manager has three different configurations in which it attempts to display all the necessary vital signs. If enough space is available, all will be displayed in their large format. If that is not possible, HR and NIBP and SpO2, if active, will be displayed large while all other will be displayed small. If enough space is still not available, all vital signs will be displayed small. The vital signs field 28 is guaranteed to be able to display all the necessary vital signs for a system fully loaded.

The reconfigurable interface of the invention also includes a waveform manager for waveform field 24 which a software process of the display processor 16 that is responsible for displaying the appropriate waveforms selected by the operator. To determine how the waveform area is organized, waveforms are assigned two different priorities: membership and location. A waveform membership priority dictates the order in which it will become a member of the set of viewable waveforms. This set is limited to six in a preferred embodiment. Its location priority dictates the order in which it will actually be displayed on the screen of display 18. Location priorities are automatically assigned based on the order the operator ranked all of the parameters in terms of importance in configuration mode. For the most part, a parameter's membership priority is closely related to its assigned location priority.

As noted above, generally no more than six waveforms can be displayed at one time. The system will allow a user to select more than six waveforms to be viewed, but waveforms with a lower membership priority will, essentially, be off the screen or not viewable. As waveforms with higher membership priorities are turned off, the lower ones will eventually become one of the set of viewable waveforms.

In a preferred embodiment, the ECG parameter is ranked as the most important parameter. Consequently, in terms of waveforms, ECG's primary lead is assigned the highest membership priority as well as the highest location priority. As long as the ECG parameter is in ready mode or operate mode, the primary lead will appear at the top of the display. Secondary leads, on the other hand, are automatically assigned the lowest membership priority but the next to highest location priority. If the secondary waveforms selected to be viewed are part of the set of viewable waveforms, they will be displayed underneath the primary lead.

The invasive pressure waveforms follow a similar pattern. The location priority of all pressure waveforms is the same and is based on the ranking of the invasive pressure parameter. Pulsatile waveforms' membership priorities are essentially the same as their location priority. However, non-pulsatile pressure waveforms' membership priorities are just higher than that of secondary ECG leads.

The CO2 parameter requires space for displaying status messages and its waveform area is a convenient and logical place for this purpose. Since most operators will want to view the CO2 waveform, a requirement may be placed on the system that it must display the CO2 waveform as long as CO2 is in operate mode or ready mode. Unlike other parameters, a menu choice is not available for turning this waveform on or off. Consequently, after the ECG primary lead, the CO2 waveform has the next highest membership priority. Its location priority is assigned based on its ranking in configuration mode.

The waveform manager must also start waveforms at the same time such that sweeps are synchronized according to the speed selected.

Figure 4:
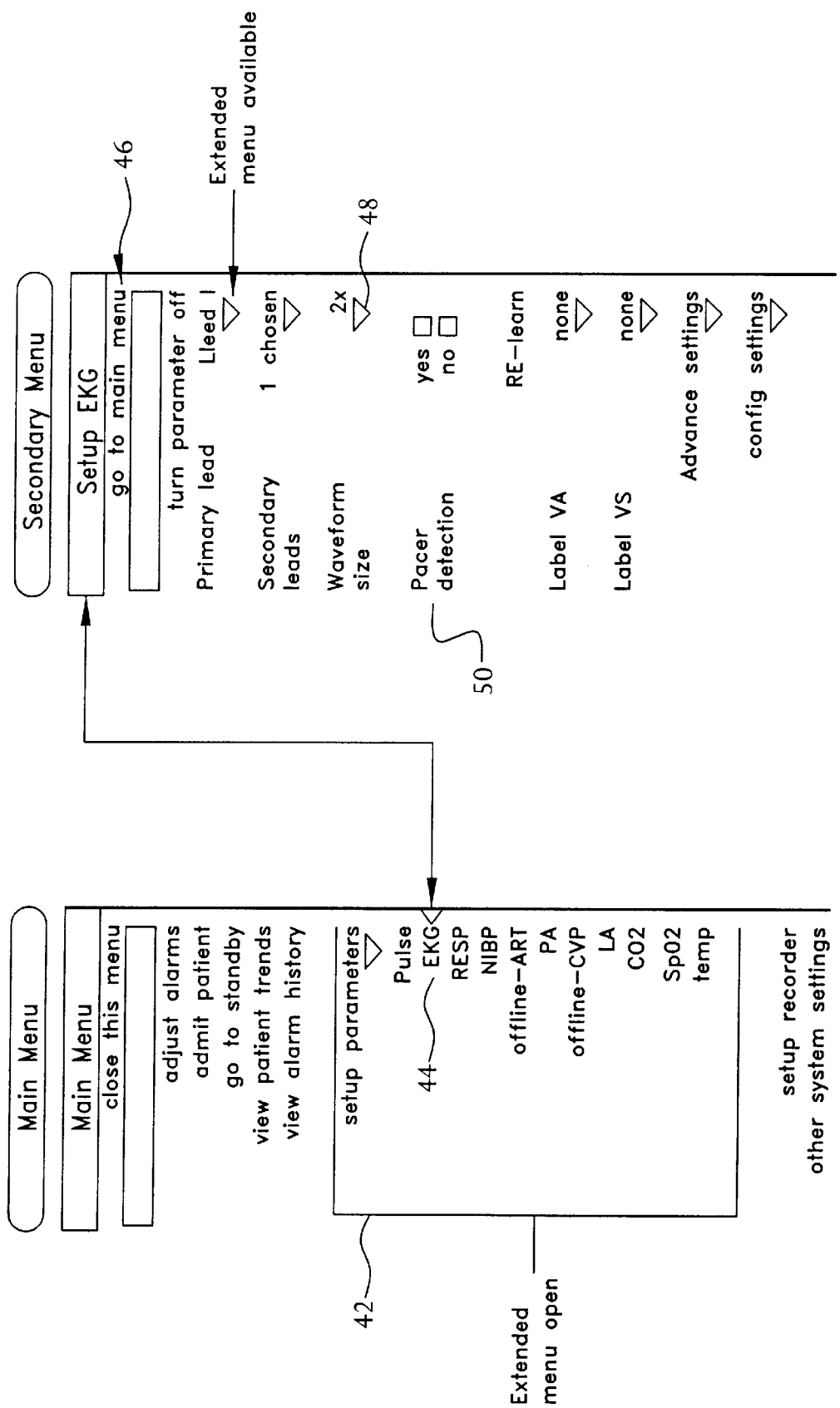
FIG. 4 illustrates the main menu and corresponding secondary menu for the EKG setup parameters mini menu.

At power up of the modular patient monitor 10, the operator is given the option of admitting a new patient via a popup window screen. If a new patient is to be admitted, an Admit Patient menu appears in the popup window. Otherwise, the main menu illustrated at the left side of FIG. 4 appears on the left side of the screen of display 18. As shown in FIG. 4, each entry of the main menu typically has a secondary menu which is accessed and displayed in place of the main menu when a selection is made from the main menu. The main menu is the primary level of operation and provides access to all secondary menus upon selection of the corresponding menu option in the main menu. The preferred embodiment of the main menu includes the following selections:

close this menu: hide the main menu and view the full waveform field 24.

flash box 34: when activated, presents a shortcut to the menu option that the display processor 16 determines is most likely to be selected.

adjust alarms: review or change alarm limits for all operating parameters.

admit patient: enter name/ID number, perform quick admission, or change patient type.

go to standby: turn sensors and alarms off but leave monitor on.

view patient trends: display accumulated data for current and/or previous patient.

view alarm history: display patient and procedural alarm histories.

setup parameters: review or change settings for monitored parameters for all currently connected parameter modules 14.

setup recorder: review or change settings for strip recorder or printer.

other system settings: turn monitor off, perform multi-parameter functions, or enter configuration or service mode.

If no menu is active, the viewing of the main menu is activated by the operator pressing or turning the select knob 20 or is automatically activated when an entry is placed in the flash box 34. On the other hand, the main menu is deactivated by the operator selecting the "close this menu" choice. This menu choice will be unavailable when the flash box 34 contains an entry. When any menu is active, the main monitoring screen displays 3.5 seconds of waveform data plus vital signs. Once the main menu is closed, the main monitoring screen will be displayed with an additional 2.5 seconds of waveform data, making a total of 6 seconds of waveform data. While any menu is active, if no operator interaction (use of the select knob 20) is detected for a period extending longer than, e.g., two minutes, any secondary menu opened and the main menu will be closed to reveal the additional waveform data.

As illustrated in FIG. 4, the first menu option on a secondary menu is preferably "go to main menu," for typically only the main menu or the secondary menu is displayed at a given time. The remainder of the options on the secondary menu are specific to the main menu selection and provide additional options for setting monitoring parameters and managing patient data. Within secondary menus, the menu choices are grouped in three categories: normal settings, advanced settings, and configuration only settings. Normal settings are menu choices that the typical operator may want to modify or adjust. The typical operator is familiar with their functionality and they are part of the minimum tool set needed by the operator to perform his or her job. When a secondary menu is opened, these are the menu choices that are initially available. Advanced settings, on the other hand, may not be familiar to the average operator. When the secondary menu is opened, these choices are initially unseen and are accessed through a mini menu titled "advanced settings." Upon selection, all the advanced settings' items or choices become available for modification. Configuration settings are settings which, after being set the first time, should never need modifying. These settings can only be modified in an off-line, password protected mode and are available usually for accommodating the differences in the standards of care between hospitals or particular departments within a hospital. These settings are only reviewable in normal operational mode and are accessed through the mini menu title "configuration settings."

All menu choices are accessible through secondary menus, and each secondary menu has its own template or table defined for the information (i.e., menu choice settings) it knows about. Consequently, a table is defined for each parameter, and each parameter has memory space available in its associated parameter module 14. One set of the patient-type specific settings of the active table is what is maintained in the parameter's memory space in the associated parameter module 14. This duplicate copy in the parameter module 14 is updated as these settings are updated in the active table maintained by the display processor 16 in operate mode. Most tables are divided into two different sections: settings that mostly effect how the data is displayed and settings that mostly effect how data is processed. Settings that mostly effect how data is processed are very much dependent on the type of patient being monitored. For each of these patient-type specific menu choices, the table is designed to hold two different settings, one for each different patient type (e.g., adult or neonate). For other menu choices, which mostly effect how data is formatted on the screen of the display 18, the table is designed to hold only one setting which is independent of patient type.

Preferably, for each secondary menu table defined, three copies of the menu choice settings table, each containing different state information, exist: factory default, operator default, and active. The factory default table includes the settings from the factory, is maintained in ROM, and is not modifiable by the operator. The operator default table is maintained in non-volatile RAM and includes the changes made by the operator in configuration mode. The active table is also maintained in non-volatile RAM and is updated every time the operator makes a change to a menu setting in normal operating (i.e., clinical) mode.

The afore-mentioned regular and advanced settings menus are always accessible. Modifications to these settings in configuration mode forces an update to settings in the operator default table. In operate mode, modifications to these settings forces an update to the settings in the active table. Since the configuration settings in each secondary menu can only be modified in configuration mode, an update to that setting will occur in the operator default table. Since these menu choices are not accessible in operate mode, their state in the active table will always be the same as their state in the operator default table. On the other hand, non-configurable menu choices (which are never presented to the operator) are not accessible in any menu and, therefore, are in no way modifiable by the operator. In this case, the state of the setting in the active and operator default tables will be the same as their factory default state.

Active tables are copied over with operator default tables whenever a new patient is admitted. An admit dialog box is presented to the operator upon power-up or return from standby. If the operator answers "yes" to the dialog in the dialog box, the operator default tables are copied onto the active default tables. If the operator answers "no," then the active tables remain unchanged. Consequently, across the cycle of power, the "monitoring state" of the modular patient monitor 10 remains unchanged. Answering "yes" to the admit dialog is thus the same as selecting the "quick admit" menu choice in the "admit patient" secondary menu off of the main menu.

The modular patient monitor 10 will recognize the difference between when a parameter module 14 is available at power up and when a parameter module 14 is connected while the system was operating normally. This difference is only recognized by the fact that the system is given some n seconds in which to "power up." Therefore, if the ON switch is pressed at t=0, from t=0 to t<=n, the system is in its "power up" state. For anything beyond that time (t>n) the system is in its normal operating state. For example, in a preferred embodiment, "n" is set to 30 seconds. When the system is operating normally and a parameter module 14 is unplugged, its active table will be maintained. At "power up," a parameter whose module is connected will be configured according to its active table.

When a parameter module 14 is connected during normal operation, the specific patient type portion of the active table in the system will be compared to the stored settings in the memory of the parameter module 14. If the patient type of the parameter module's copy does not match the current patient type for the system, the system's active table for that parameter will not be used. On the other hand, if the patient type matches but any one of the settings stored in the parameter module's memory is out of range, the system's active table for the parameter will be used. Otherwise, if they do not totally agree, the operator will be prompted to select which settings to use, the system's copy or the parameter module's copy. A parameter menu's active table, whether its module is connected or not, will be reset to the operator default table when a new patient is admitted.

Figure 5:
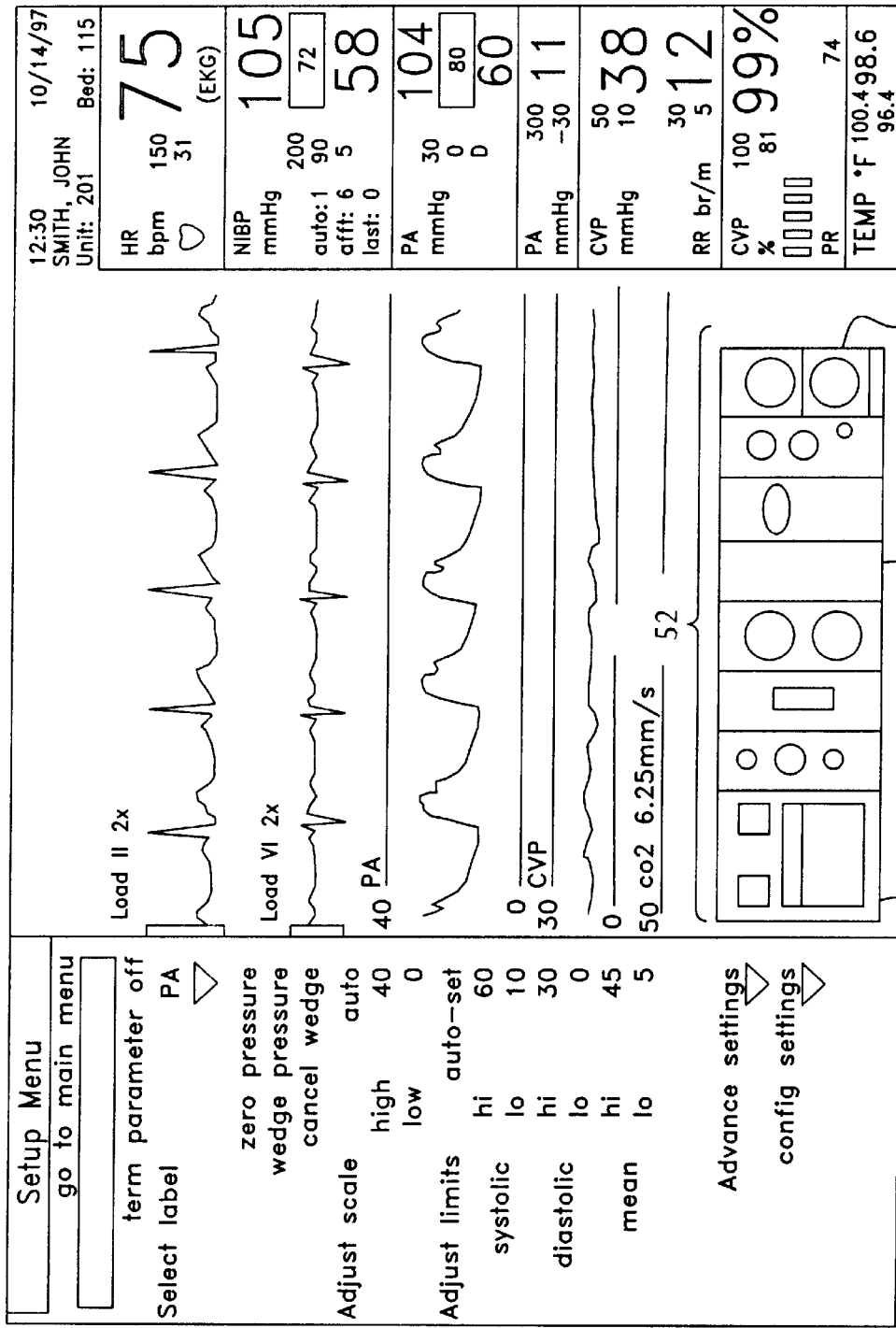
FIG. 5 illustrates the graphics of the patient module and the connected parameter modules.
Figure 6:
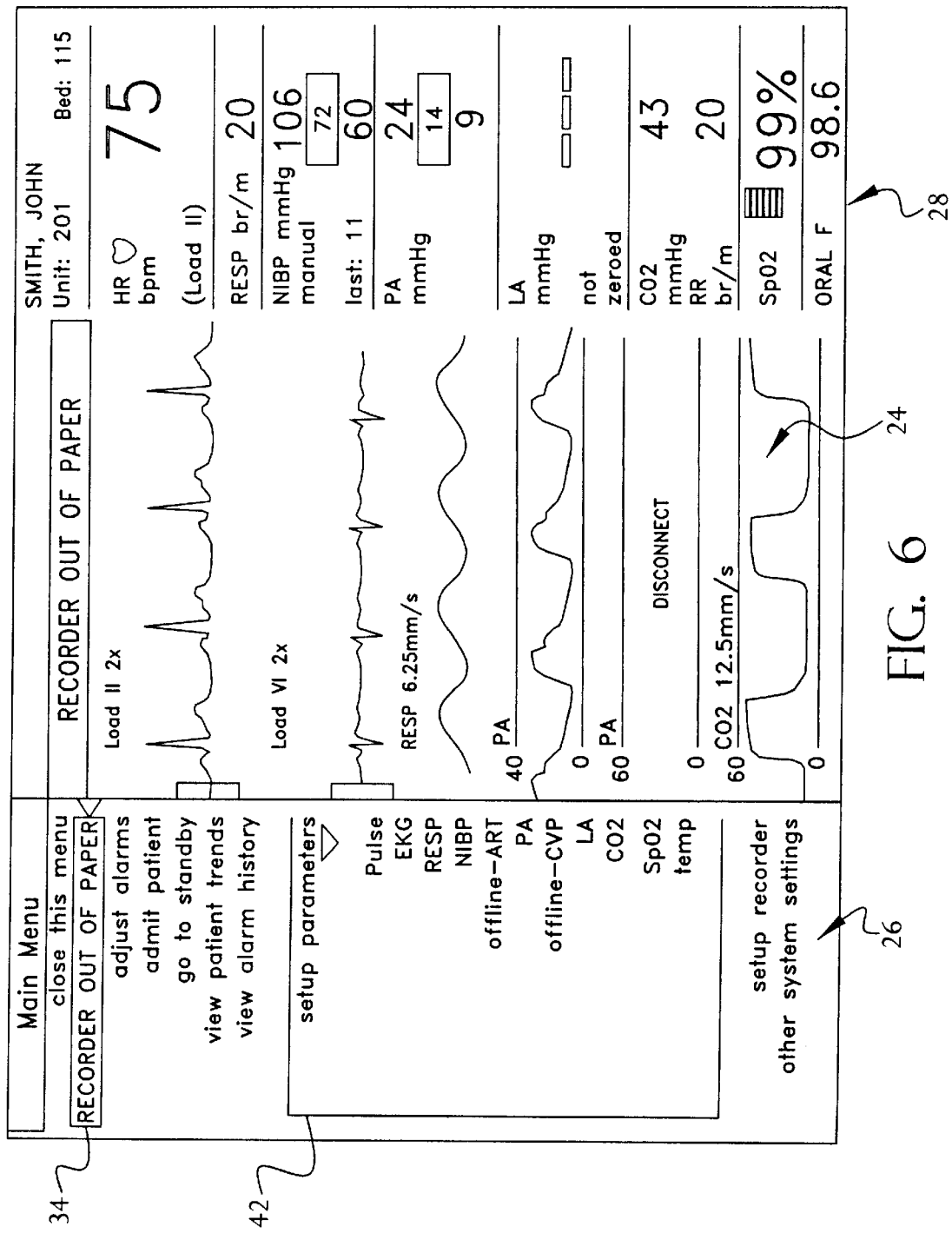
FIG. 6 illustrates the main menu with an active flash (select) box indicating that the recorder module is out of paper.

In the preferred embodiment of the reconfigurable interface of the invention, the reconfigurable user interface can graphically show the operator what parameter modules 14 the system knows are connected. As shown in FIG. 5, for each different parameter module 14, a graphic 52 is displayed that preferably represents the features of the parameter module 14. For example, graphic 54 is a recorder module. Depending on what parameter modules 14 are currently connected, a graphic for each parameter is overlayed onto a graphic of the main housing 12. Empty slots 57 within the main housing 12 should show up as blank areas on the graphic 52 of the main housing. Since a secondary menu should exist for each parameter connected, when the graphic is displayed when a particular parameter's menu is opened, the graphic of the sensor associated with that parameter should be highlighted. This is very useful for some parameter modules such as invasive pressure where two logical invasive pressure parameters may exist in a single parameter module and that parameter's parameter module 14 can be plugged into any slot within the main housing 12. This prevents the use of any type of numbering scheme. For parameters in which the system must recognize multiple instances, this graphic is necessary to associate the menu instance of the parameter with a particular connector 56 on a particular parameter module.

As illustrated in FIG. 4, the menuing system of the invention is designed to occupy the menu field 26 and resembles a "to do" list of vertically listed items. Most menus are accessed and menu options selected using the select knob 20. For example, select knob 20 may be turned clockwise to move a triangular shaped pointer 36 up the menu and counterclockwise to move pointer 36 down the menu (or vice-versa). When setting a value, the pointer 36 remains stationary at the setting being adjusted, and clockwise rotation of select knob 20 increases the value while counterclockwise rotation of select knob 20 decreases the value. Pushing in select knob 20 selects or confirms the menu option currently pointed to by pointer 36. In this fashion, the operator may select menu options which make it possible to answer questions, choose one or more items from a list, and/or adjust values such as alarm limits.

The menu may contain several types of menu items. For example, a link item 44, when selected, opens a secondary menu and is found only in the main menu. A single action item 46 in the menu presents the operator with a single item that can be selected or ignored. Upon selection, the system performs the desired action. Arrow items 48 are used in any choices that expand to show more choices or items in an expanded menu. Selection of an arrow item 48 causes an expandable menu choice to open to display its other items. Reselection of the arrow item 48 causes the menu choice to close or to be displayed in its collapsed state. An adjuster item is used to set a value, where rotation of select knob 20 changes or adjusts the indicated value. A dialog item opens a modal dialog box, while a data entry dialog item opens a data entry dialog box. A radio button item 50 presents the operator with two or more items from which only one item may be selected. Preferably, a radio button menu choice 50 does not automatically close upon confirmation so that the operator may see the new selection in effect before determining if it is the correct setting. Also, check box items allow the operator to select multiple items from a list of two or more items.

Menu items can be combined to create other types of menu choices which may be needed to fit a particular application (except that radio button items may not be combined with check box items in the same list). For example, one common choice in many of the secondary parameter menus is means for setting the alarm limits for one of the parameter's derived vital signs. In particular, for each vital sign, the operator needs the ability to set its high limit, its low limit, or have the system automatically set both based on the patient's current condition. To accomplish this, an autoset choice is created which consists of a single action item whose text contains the label of the associated vital sign and "autoset" followed by two adjusters which can be manually adjusted to the desired limits. The system will automatically set the limits if the operator selects the "autoset" single action item, whereby the system calculates the new high and low limits based on the currently derived value for that vital sign and updates the high and low adjuster items accordingly. On the other hand, the operator can manually adjust the limits using the adjuster menu items.

As noted above, mini menus may be used as an alternative to opening an entirely new menu level when it is more logically expedient to remain within the current menu level (since only one menu is displayed). The mini menu is an expandable menu choice that contains an arrow item and a group of menu items or choices. When the mini menu is closed, only the arrow item 48 is visible; however, when the mini menu is selected, all choices below the arrow item 46 are pushed downward to make room for the items or choices part of the mini menu. For example, the afore-mentioned Setup Parameters mini menu 42 provides links to secondary menus for the currently connected parameters so that the operator may select the settings for the indicated parameter. Since any number of parameter modules 14 may be connected, the available links to secondary setup menus are based on the current parameter modules 14 which are connected. Also, the number of parameters that the system may monitor at a given time is only limited by its ability to display all the necessary information on the display 18 at the same time. As a result, the main menu may be required to contain a large number of links to parameter secondary menus at once. Preferably, if the number of parameters being monitored will not cause the main menu to extend off the bottom of the display 18, the mini menu 42 remains open as in FIG. 4. Otherwise, the mini menu 42 will be closed.

The reconfigurable user interface of the invention is designed to allow the operator to explore. One way this is accomplished is by not making the menuing system modal. In other words, except when necessary, the operator is not forced to make a decision (i.e., press the select knob 20) before continuing use of the menu. The interface is not modal in that, when a choice is opened or expanded, another choice can be selected. Upon selection, the new choice will open and the previously selected one will close automatically with no change to the setting. In a similar way, when a group of menu choices is visible (e.g., in a mini menu), another menu choice or group of choices outside of the group can be opened. Upon selection, the previously opened group will first close any menu choice within it that was opened, again with no change to its setting, and then close itself. In addition, at the top of every secondary menu is an option to exit that menu so that the operator is never forced to make a change to the current setting under examination. An exception is that when the operator has entered a value adjustment box, the operator must press the select knob 20 to confirm the value (whether or not changed) before being able to exit the menu. In other cases where the system operation does require the operator to make a choice, it is preferably presented in a dialog box. For example, in FIG. 6, when the operator selects the recorder out of paper alarm, a dialog will appear with instructions on how to load the paper.

In accordance with a feature of the menuing system of the invention, means are provided for making a choice or item that is viewable within the menu unavailable for selection. Pointer 36 will point to an unavailable menu choice but, if selected by the operator, a negative acknowledgment sound will be generated, and the help line 32 will give the operator a reason why the choice is unavailable. Unavailable items may be differentiated by color or brightness, which is much less intrusive than constantly changing the menu size by adding or removing items and choices.

Flash (select) box 34 is another feature of each menu of the user interface of the invention. As shown in FIG. 2, the flash box 34 is typically a blank rectangle in the menu reserved for the display of certain asynchronous events. When flash box 34 is inactive, the pointer 36 skips over it. Flash box 34 becomes active in response to asynchronous events such as system alarms. Once the flash box 34 is activated, a flashing message appears in the rectangle and the flash box 34 may be navigated by the pointer 36. Preferably, flash box 34 may contain more than one entry, but it should only display one entry at a time. It operates according to a first in, first out methodology whereby the next oldest entry is displayed when the oldest entry is removed. To remove an entry from the list of active items, the operator must address the currently displayed entry.

In the simplest case, an asynchronous event that uses the flash box 34 is an "OK-able" alarm that activates flash box 34. These alarms can be "OK-ed" by the operator who turns them off until the system is re-armed to detect them once again. When such an alarm occurs, it appears in the flash box 34. The alarm may, by pressing on it with the select knob 20, be shut off. By turning off an alarm in this way, the audio does not need to continue to sound for a condition that the operator knows to exist. As another example, if a parameter module 14 with a parameter in operate mode or ready mode is unplugged from the main housing 12, an alarm will be generated and a message to that effect will be displayed in the flash box 34. Okaying the message in the flash box 34 will remove the alarm.

In some circumstances where the flash box 34 is selected by the operator, a pertinent menu or popup window appears at the bottom of the screen of display 18. The operator then follows any instructions in the menu or popup window and presses the select knob 20 to close the menu or popup window and to return to the full screen.

Another use of flash box 34 is to provide a means for navigating through the menu system with a lesser number of steps and, at the same time, assist the user with the particular steps that must be followed to complete a particular task. For example, when an arterial pressure sensor is initially connected, it must be zeroed. Hence, when the system detects that a pressure transducer has been plugged in, the main menu is opened with the pointer 36 positioned next to the flash box 34 and the message "ART" blinking within it. The operator then pushes select knob 20 to select the "ART" message. In response, the system brings up the ART secondary menu with the pointer pre-positioned at "zero transducer." One more press of the select knob 20 and the zeroing operation is performed. Generally, if a secondary menu is entered from a flash box 34 entry in this fashion, the pointer 36 should be positioned pointing to the choice that will service the flash box 34 entry.

Figure 7:
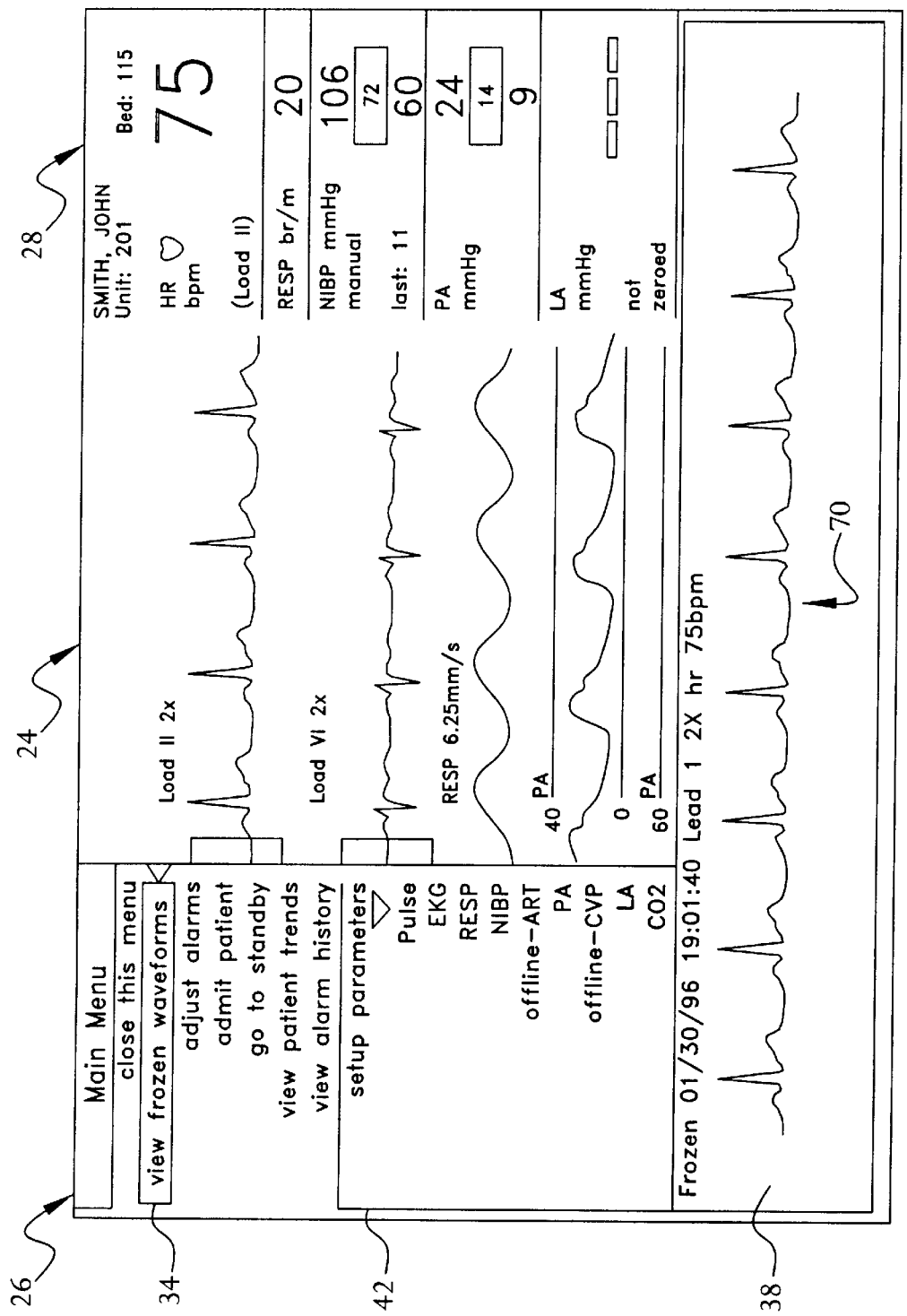
FIG. 7 illustrates the main menu with an active flash (select) box indicating that more frozen waveforms can be viewed.

As shown in FIG. 7, the flash box 34 is also activated when the freeze waveform data hardkey 22 is selected. The message "view frozen waveforms" appears in the flash box 34 for selection of the view frozen waveforms secondary menu. The operator may then select the frozen waveforms to view from a list of menu options and may select a frozen waveform to print at the recorder parameter module 14. As shown, a frozen waveform appears in popup window 38, and an arrow 70 appears in the middle of the popup window 38 to indicate the midpoint of the waveform data.

Dialog boxes are opened in dialog window 38 and are of several types including modeless, modal, and alert. Modeless dialog boxes should be used to get user input that is preferred but not required. The responses for this type of dialog should be yes or no. The yes/no question should be displayed in the dialog and the pointer should default to the "no" response. If the operator does not respond within a certain length of time, "no" becomes the accepted answer. By answering "no", the state of the modular patient monitor 10 should remain unchanged. However, if it is not possible to continue operation without changing the state of the system, this type of dialog should not be used. Modal dialog boxes, on the other hand, should be used to force the operator to make a choice before the system will continue with the current operation. In other words, the operator should not be able to access any other menu functions until he or she responds to the dialog box. The two responses for this type of dialog should be yes or no, and the question should be presented to the operator as a yes/no question.

A modal dialog box should also be used in situations where more information needs to be provided to the operator than can be communicated through the menu. This information is necessary but not critical to the proper operation of the system. The only response to this type of dialog should be "OK." A dialog box of this type is only accessed by placing a message in the flash box 34. When the operator selects the message in the flash box 34, the necessary information is presented to the operator with the pointer pointing at the "OK" response. Confirmation of the "OK" response will move the dialog box and allow other menu settings to again be accessible.

Alert boxes, which are a type of modal dialog box, should be used to inform the operator of error conditions that should be responded to before continuing any other interaction with the system. The only response to this type of dialog is again "OK," and the necessary information is presented to the operator with the pointer pointing to the "OK" response. The operator must confirm this response before the dialog box will be removed and the operator may again access any other menu settings. This type of dialog box is automatically presented when a fatal error condition occurs.

A data entry dialog box allows the operator to enter text, for example a patient's name, into the system. The data entry dialog is a modal dialog contained in the dialog field 38 and offers the operator the ability to select any letter in the alphabet, a few select punctuation marks, and the numbers 0 through 9. To select a character, the pointer is moved to the desired character or number and the select knob 20 is pressed. An option such as DONE or CANCEL can be selected to close the dialog window.

The menuing manager is a software process of display processor 16 which controls the afore-mentioned menuing activities displayed in the menu field 26.

Generally, the menuing manager manages two tightly coupled, but independent activities operated on the display processor 16. The first component provides the actual user interface and user event generation. The second component processes these user interface events and other events generated in other system components.

Events can be generated by virtually any component in the modular patient monitor 10. These events are queued up into one of two distinct queues. One is processed by a main event dispatcher (the action queue). The second is handled by a menu event dispatcher (the event queue). A second dispatcher and queue dedicated to the menuing system provides better user responsiveness as this queue can be given higher priority. All events have the same basic format and include three common fields. These are the event type, the event action, and a data field. Other fields may be present and are interpreted based upon the event action. The event type is used by the dispatcher to route the event to the proper system component. The action is used to convey what has happened (the actual event), and the data is a common, 32 bit wide, field specific to the event type and event action fields, usually the object receiving the event.

In a simple operator interaction, such as pressing the select knob 20, an event would be generated by the keypad manager and deposited into the menu's queue (the event queue). The menu manager's dispatcher would dequeue the event and route it to the currently opened menu. The menu would send the event into the menu system where it is routed to the current control (radio button, adjustor, etc.). The control would either change its state or generate an event into the main event queue (the action queue).

In a preferred embodiment of the invention, the menuing manager manages a hierarchical collection of objects called MenuItems. These MenuItems fall into three categories:
1) Simple: Terminal items, Link items, Radio Button items, and Check Box items;
2) Complex: Adjustors, Fuel Gauge, Yes/No items; and
3) Group: Group, Scroll Group, mini menus, etc.

The Simple menu item is a menu item that only processes the knob press events generated when the select knob 20 is pressed. These controls either deposit an event into the action queue or cause the menuing system to change state (close a menu, open a different menu, close a mini menu, etc.). The Complex menu items can interpret KNOB_UP (when select knob 20 is rotated clockwise) and KNOB_DOWN (when select knob 20 is rotated counterclockwise) events as well as the KNOB_PRESS event. With the Adjustor and Fuel Gauge items, the KNOB_UP and KNOB_DOWN events modify the value of the control. The Group menu item maintains a list of MenuItems and handles navigating the pointer 36 through the list, display and computing heights of the MenuItems, and tasks related to organizing a collection of items.

All items appearing in a menu are derived from the MenuItem class. A given MenuItem is responsible for processing select knob events passed to it. The MenuItem is also responsible for knowing specifics about itself such as its height, how to draw itself on the screen, if it is the active control. Knowledge of these attributes allows substantial flexibility in the positioning, ordering, and general presentation of groups of these items. The MenuItem's attributes and use include:
1) Pointer location: indicates where in the MenuItem the pointer should be positioned if the item is current.
2) Availability: indicates whether the current MenuItem can receive the KNOB_PUSH event.
3) Help Lines: those lines communicated to the Help Line field 32 when the item is pointed to or changes state.
4) Height: used by whatever group contains this item to determine how much room to give it on the screen of the display 18.
5) Priority: used by the group to determine actual placement order of the MenuItems on the display 18.

These controls can exist in one of 4 states with transition occurring on a press of select knob 20. These states are:

| | |
|---|---|
| Navigate | Moves pointer up/down through menu choices. |
| Select | Activates a control causing it to send an event (most controls) or change state (Adjustor and Fuel Gauge). |
| Adjust | Modifies the value of a control. Adjustors and Fuel Gauges only. |

-continued

| | | |
|---|---|---|
| Confirm | | Accepts the value in a control and generates an event. Adjustors and Fuel Gauges only. |

The Group menu item is a MenuItem that can contain one or more MenuItems. The group manages cursor movement, location computation, and drawing among the MenuItems it groups together. Since the Group is, itself, a MenuItem, groups may contain other Groups. The following chart outlines the different types of Groups and their uses.

| Control | Base Class | Use |
|---|---|---|
| Group | MenuItem | Manages location, navigation, and presentation of one to 40 unrelated MenuItems |
| mini menu | Group | Adds opening and closing ability as in the Choice, and draws itself different in each state. |
| Scroll Group | Group | Provides scrolling ability if group extends beyond the screen area. This should be the top level group in any and all menus. |
| Choice | Group | Adds ability to open and close the control when first item in the control is selected. Not required to, but usually contains a homogeneous collection of MenuItems. |
| RBChoice, ASChoice, CBChoice, MMChoice, PSChoice | Choice | Manages interaction between the various controls contained in the choice. Each control should only contain MenuItems it was designed to contain. RB = Radio Button, AS = AutoSet, CB = CheckBox, MM = Mini Menu, PS = Parameter Setup |

The Group menu item is responsible for maintaining the list of MenuItems it contains and placing each in its area when necessary. When asked to place and display its MenuItems, the Group scans the list positioning each item based upon the heights returned by the MenuItem. In this way, the individual MenuItems which can change size on their own are drawn properly, if the menu is told to recompute object position. The Group menu item also maintains which of its items is current. This only applies to one level, though. For instance, if a Group contains a mini menu, the Group only knows that the mini menu is current, not which control within the mini menu is current. That responsibility befalls the mini menu.

Scrolling is handled by polling the current control to decide if it lies completely on the screen. The control is given an offset value to subtract from its vertical coordinates and determines it if it is completely visible. If it is not completely visible, it returns to the Scroll Group the offset of its top and bottom. The Scroll Group then adjusts the offset to place the control at the top of the menu (if scrolling up) or at the bottom of the menu (if scrolling down).

The various Choice derived controls coordinate behaviors that require more than one MenuItem to respond to an event. For instance, the Radio Button Choice control detects if a given Radio Button is selected and deselects the other Radio Buttons. It also provides controls that allow the software to change the current control in response to various system events.

The Complex controls are MenuItems that additionally respond to KNOB_UP and KNOB_DOWN events. Six complex controls are implemented, their descriptions follow:

| MenuItem | Base Class | Description |
|---|---|---|
| Adjustor | MenuItem | Allows adjustment and selection of a numeric value within a specified range |
| Fuel Gauge | Adjustor | Same as Adjustor but adds visual representation of current value relative to entire range |
| Yes/No item | Terminal item | Offers a Yes and No choice for a particular option |
| Limit item | Terminal item | Contains two adjustors for high and Low alarm limits |
| AutoLimit item | Terminal item | Limit item that can be auto-set |
| Top Control | MenuItem | Collects the Close item and Magic item (see next section) into one item. Only one of these owned by the Menu. |

On the other hand, the Simple controls are those MenuItems that react to KNOB_PRESS events only. The control can have three different responses (or combinations of these) to an event. It may either change its state (Check Box, Radio Button), post an event (all controls except the Link item), or cause the Menu to change its state (Link, Arrow item). A table of the Simple Controls follows:

| MenuItem | Base Class | Description |
|---|---|---|
| Terminal item | MenuItem | Generates a fixed event when selected |
| Check Box | Terminal item | Generates a fixed event and changes appearance |
| Radio Button | Terminal item | Generates a fixed event, changes appearance, tells its Group to deselect other radio-buttons |
| Arrow item | Terminal item | Terminal item that displays an empty or filled down arrow against the right margin. Used for mini menus, etc. |
| Close item | Terminal item | Does not send event, tells Group (usually a Scroll Group) to close itself |
| Dialog item | Terminal item | When selected, activates a Dialog Box |
| Link item | Terminal item | When selected, tells Group to cause new menu to open |
| Magic item | MenuItem | Maintains a prioritized list of MenuItems that are to be displayed in the flash box |

The flash box 34 is implemented using the Magic item control. This control maintains a list of MenuItems. As a MenuItem itself, this control can be, and is, displayed in the menu and acts just as a Terminal item or Radio Button item concerning user interaction. When selected, it removes the current MenuItem from its list, and either opens the menu the MenuItem points to, or generates the event it contains (or both). Additionally, the Menu polls the Magic item to decide if there are any active Magic Entries and refuses to close the main menu if there are.

There is only one menu present in the system. That menu contains the one and only Top Control and the currently active Scroll Group. These differing Scroll Groups are what the operator perceives as the different menus. This menu is the entry point of events from the menu manager. This menu also processes the messages from the Link items and the Close item instructing the menu to close or present a different Scroll Group. It initiates recompute sequences (determines the location of each MenuItem in the menu), repaint sequences (draw the entire menu), and other actions. This item also controls the text at the top of the menu, the border around the menu, and the actual drawing of the pointer.

The menu manager further provides a traditional C language interface to the C++ menuing system. It also maps some key events and system Dialog Boxes.

The reconfigurable user interface of the modular patient monitor 10 may be adapted for other products for which a similar look and feel is desired by using Product Specific Menus (PSMs). PSMs are created as specializations of the Scroll Group. As specializations, they receive key, knob, and other events immediately after the menu, but before any other processing is done. This allows the PSMs to filter, modify, or generate additional events for the menuing system, though this is usually not necessary. In the usual case, the PSM creates the various MenuItems that it needs and assembles them into the desired structure. This is done from the "bottom-up." For a given PSM, the lowest controls (say several Radio Buttons) are created and events are assigned. These controls are then added into the next level control (e.g., a mini menu). Finally, the PSM adds the top level controls into itself. At this point, the menuing manager takes over and handles the display and navigation of the menu.

The PSM can also specialize the event processing service (ProcessEvent( )). This service is called by the menu class when an event is received. Specializing this service will allow the PSM to receive events if it is active and process these events appropriately. All key and knob events are first passed to the currently active PSM. That PSM should either act upon the event or pass it to the Scroll Group's process event service if it does not recognize the event or does not want it. All events not recognized as menu events or as Key/Knob events are passed to the main PSM (called "main menu"). That PSM may pass the event to the proper inactive PSM or processes it itself.

Based on the above description of the reconfigurable user interface of the invention, those skilled in the art will appreciate that the user interface selectively populates the menus and displays waveform and vital signs information based on the parameter modules 14 which are plugged in at any given time. Due to event processing, when a parameter module 14 is added or removed, the reconfigurable user interface is updated immediately.

The reconfigurable user interface of the invention is also particularly easy to use in that a so-called flash box provides shortcuts in response to asynchronous events such as alarms and the like. The flash box also assists the operator with the particular steps that must be followed to properly setup or operate a particular feature of the system.

In addition, since the menus of the reconfigurable user interface of the invention are not modal, an operator may navigate the menus without making any selections or changing the state of the device.

Although an exemplary embodiment of the invention has been described in detail above, those skilled in the art will readily appreciate that many additional modifications are possible in the exemplary embodiment without materially departing from the novel teachings and advantages of the invention. For example, those skilled in the art will appreciate that different parameter default configuration tables may be stored for different environments, such as operating room or emergency room, and downloaded from a personal computer or another patient monitor. Accordingly, these and all such modifications are intended to be included within the scope of this invention as defined in the following claims.

What is claimed is:

1. A modular patient monitor including a reconfigurable user interface which displays patient parameter data for each patient parameter for which patient monitoring is activated, comprising:

a display which displays patient parameter data;

a parameter interface which determines the patient parameters for which patient monitoring is activated and which accepts patient parameter data for presentation on the display; and a display processor which processes said patient parameter data from said parameter interface to determine which and how many patient parameters need to be displayed on said display, which allocates space on said display for at least one of vital signs and waveform data associated with the patient parameters to be displayed, and which monitors said parameter interface so as to reallocate space for presentation of said patient parameter data on said display when said patient parameter data is detected at said parameter interface in accordance with parameter settings based on operator preferences regarding the appearance on said display of at least one of said vital signs and waveform data associated with said patient parameters, said space reallocation occurring when at least one of a number and a type of patient parameters is changed during operation of said modular patient monitor, and wherein said display processor further includes a menu manager which presents menus to said display for user navigation and which updates menu selection options in said menus when said parameter interface, which is monitored by said display processor, provides an indication that a patient parameter has been activated or deactivated, and wherein each menu contains a flash box which flashes a most likely menu selection item for selection from said menu in response to an asynchronous patient monitoring event detected by said parameter interface, and wherein, in response to said asynchronous patient monitoring event, said menu manager places a menu selection cursor at said flash box for selection of said most likely menu selection item without further cursor movement by the user.

2. A patient monitor as in claim 1, wherein a parameter setup secondary menu is added as a menu selection option when an associated patient parameter is activated and is removed as a menu selection option when the associated patient parameter is deactivated.

3. A patient monitor as in claim 2, wherein said menu manager enables navigation of said menu and secondary menus without selecting any menu selection items or changing operating modes of said patient monitor.

4. A patient monitor as in claim 1, wherein said asynchronous patient monitoring event is a condition of said monitor requiring operator attention and said most likely menu selection option is a menu selection option which services said condition.

5. A patient monitor as in claim 1, further comprising a parameter module which plugs into a main housing of said patient monitor containing said display processor so as to activate a patient parameter associated with said parameter module, wherein said display processor displays a graphic of said patient monitor on said display and overlays on said graphic of said patient monitor a graphic of each type of parameter module which is plugged into said main housing.

6. A patient monitor as in claim 5, wherein a graphic of a sensor associated with an activated patient parameter is highlighted when an operator is setting parameter settings for said activated patient parameter.

7. A patient monitor as in claim 1, wherein each patient parameter has a parameter settings table which specifies factory default, operator default, and active parameter settings regarding the appearance on said display of at least one of said vital signs and waveform data associated with that patient parameter.

8. A patient monitor as in claim 7, wherein the operator default parameter settings are set by an operator in a display configuration mode and said active parameter settings are set by an operator during active monitoring of a patient.

9. A patient monitor as in claim 8, further comprising a parameter module which plugs into a main housing of said patient monitor containing said display processor so as to activate a patient parameter monitored by said parameter module, wherein a copy of said parameter settings table for said activated patient parameter is stored in a memory of said parameter module and in a memory of said main housing, said display processor prompting an operator to select which parameter settings to use when the active parameter settings for said patient parameter stored in said memory of said parameter module and in said memory of said main housing do not match.

10. A patient monitor as in claim 9, wherein said active parameter settings are stored in said memory of said main housing when said patient monitor is turned off, and said patient monitor uses the stored active parameter settings when said patient monitor is turned back on.

11. A patient monitor as in claim 10, wherein said operator default parameter settings are copied over said stored active parameter settings in response to an operator initiated event.

12. A patient monitor as in claim 11, wherein said operator default parameter settings include an operator's priority of the importance of respective patient parameters for display, wherein said display processor presents at least one of vital signs and waveform data associated with higher priority patient parameters more prominently on said display.

13. A patient monitor as in claim 12, wherein said waveform data is sorted by membership priority in a set of waveforms to be displayed and by location priority whereby higher priority waveforms are displayed at a more prominent position on said display.

14. A patient monitor as in claim 1, further comprising a queue which holds a plurality of said asynchronous patient monitoring events for handling by said menu manager in a first in, first out fashion.

15. A patient monitor as in claim 7, wherein said parameter settings table comprises separate factory default settings for each said parameter for each environment in which said modular patient monitor is used.

16. A patient monitor as in claim 7, wherein said parameter settings table for each patient parameter is downloaded from one of a personal computer and another patient monitor.

17. A patient monitor as in claim 1, further comprising a select knob by which an operator may navigate said menus, said select knob moving a pointer in said menus and selectively adjusting said parameter settings in said menus to said operator preferences by rotation of said select knob.

18. A patient monitor as in claim 17, wherein said select knob is rotated to move said pointer to a parameter settings adjustment box in a menu, and upon selection of said parameter settings adjustment box from said menu, said select knob is rotated to selectively adjust said parameter settings to said operator preferences until said a parameter settings value is confirmed.

19. A patient monitor as in claim 18, wherein said parameter settings adjustment box is selected and said parameter settings value is confirmed by pressing said select knob.

20. A patient monitor as in claim 18, wherein said operator preferences of said parameter settings are numeric values within a specified range.

* * * * *